United States Patent [19]

Stern

[11] Patent Number: 5,597,901
[45] Date of Patent: Jan. 28, 1997

[54] HOMOGENEOUS HUMAN INTERLEUKIN 2

[75] Inventor: Alvin S. Stern, Passaic Park, N.J.

[73] Assignee: Hoffmann-La Roche Inc., Nutley, N.J.

[21] Appl. No.: 450,508

[22] Filed: May 25, 1995

Related U.S. Application Data

[60] Continuation of Ser. No. 653,165, Sep. 24, 1984, which is a division of Ser. No. 418,927, Sep. 16, 1982, Pat. No. 4,490,289.

[51] Int. Cl.$^6$ ..................................................... C07K 14/55
[52] U.S. Cl. .......................... 530/351; 530/412; 530/416; 424/85.2
[58] Field of Search ..................................... 530/350, 351, 530/412, 416; 424/84, 85.2; 514/2, 8

[56] References Cited

U.S. PATENT DOCUMENTS 4,778,879  10/1988  Mertelsmann ........................... 530/351
4,925,919   5/1990  Mertelsmann ........................... 530/351

OTHER PUBLICATIONS

Welte et al. (1982) Journal of Experimental Medicine vol. 156 (2) pp. 454–464.

Mochizuki et al. (1980) Journal of Immunological Methods, vol. 39(3) pp. 185–201.

*Primary Examiner*—John Ulm
*Assistant Examiner*—Prema Mertz
*Attorney, Agent, or Firm*—George W. Johnston; William H. Epstein

[57] ABSTRACT

Human interleukin 2 (IL-2) derived from induced human malignant cells has been purified to homogeneity using multiple high performance liquid chromatography (HPLC) steps. The purified IL-2 exhibits potent activity promoting the long-term in vitro culture of antigen-specific effector T-lymphocytes and in modulating lymphocyte reactivity.

2 Claims, No Drawings

HOMOGENEOUS HUMAN INTERLEUKIN 2

This is a continuation of application Ser. No. 06/653,165, filed Sep. 24, 1984, which is a divisional of Ser. No. 06/418,927, filed Sep. 16, 1982, now U.S. Pat. No. 4,490,289.

BACKGROUND

IL-2 is a soluble protein which is capable of modulating lymphocyte reactivity and promoting the long-term in vitro culture of antigen-specific effector T-lymphocytes (mitogenesis) and, in the past, has been produced by stimulating mouse, rat or human lymphocyte cells with a mitogen. For instance, Morgan et al. in "Selective in vitro Growth of T Lymphocytes from Normal Human Bone Marrows", 193 *Science* 1007 (1976) and Ruscetti et al. in "Functional and Morphological Characterization of Human T Cells Continuously Grown in vitro", 119 *The Journal of Immunology* 131 (1977), both discussed a process for culturing pooled normal human lymphocytes in Roswell Park Memorial Institute (hereafter "RPMI") medium containing autologous serum and the mitogen phytohemagglutinin (hereafter "PHA").

Gillis and Smith, in "Long Term Culture of Tumor-Specific Cytotoxic T Cells", 268 *Nature* 154 (1977) reported preparing murine IL-2 by stimulating normal DBA/2 mouse spleen cells with the mitogen concanavalin A (hereafter "Con A") in an RPMI 1640 culture medium containing fetal calf serum (hereafter "FCS").

Farrar et al. in "Biological Relationship of Thymocyte Mitogenic Factor and Factors Enhancing Humoral and Cell-Mediated Immune Responses" 121 *The Journal of Immunology* 1353 (1978), also disclosed preparing IL-2 from murine spleen cells incubated with Con A in a tissue culture medium containing normal mouse serum (hereafter "NMS").

Gillis et al. reported generating IL-2 from murine and rat spleen cells cultured in a RPMI 1640 tissue culture medium supplemented with heat-inactivated FCS, penicillin-G, and gentamycin. The murine and rat spleen cells were stimulated by various mitogens including Con A, PHA, and pokeweed mitogen (hereafter "PKM"), "T-Cell Growth Factor: Parameters of Production and a Quantative Microassay for Activity", 120 *The Journal of Immunology* 2027 (1978).

IL-2 has also been prepared from human peripheral blood mononuclear cells by culturing the cells in RPMI 1640 medium supplemented with autologous human serum, penicillin, gentamycin, fresh L-glutamine, and PHA. Gillis et al., "Biochemical Characterization of Lymphocyte Regulatory Molecules-II. Purification of a Class of Rat and Human Lymphokines", 124 *The Journal of Immunology* 1954 (1980)

Gillis et al. in "Biochemical and Biological Characterization of Lymphocyte Regulatory Molecules-III. The Isolation and Phenotypic Characterization of Interleukin-2 Producing T Cell Lymphomas", 125 *The Journal of Immunology*, 2570, (1980), identified the preparation of IL-2 from T cell leukemia and lymphoma cell lines, specifically a radiation-induced splenic lymphoma from the B10.BR mouse (LBRM-33) cultured in RPMI 1640 supplemented with heat inactivated FCS, $2.5 \times 10^{-5}$M 2-mercaptoethanol, N-2-hydroxy-piperazine-XI$^1$XI -2-ethene-sulfonic acid (hereafter "Hepes") buffer, penicillin, streptomycin and fresh L-glutamine. The cultures were stimulated with various mitogens including II Con. A, and PHA.

IL-2 purified from these mouse, rat and human normal T-lymphocytes, has been. found to retain different types of biological activity, including: 1) marked enhancement of thymocyte mitogenesis, Watson et al., "Biochemical and Biological Characterization of Lymphocyte Regulatory Molecules-I Purification of a Class of Murine Lymphokines", 150 *Journal of Experimental Medicine* 849, (1979) and Gillis et al. supra, 124 *Journal of Immunology* 1954 (1980); 2) promotion of long term in vitro proliferation of antigen specific helper or killer T cell lines, Gillis et al., supra, 268 Nature 154 (1977) and Watson, "Continuous Proliferation of Murine Antigen Specific Helper T Lymphocytes in Culture", 150 *Journal of Experimental Medicine* 1510 (1979); and induction of cytotoxic T lymphocyte (hereafter "CTL") reactivity and plaque-forming cell responses in cultures of nude mouse spleen cells. Watson et al., supra, 150 *Journal of Experimental Medicine* 849 (1979) and Gillis et al., supra, 124 *The Journal of Immunology* 1954 (1980). Accordingly, these identified biological activities of IL-2 indicate that IL-2 is useful in elevating immune responses and restoring immune deficient T cell populations (nude mouse spleen cells) to normal levels of cell and humoral immunity. Furthermore, these results suggest that IL-2 production and response are important parameters of immunelogical functions which may be useful in clinical diagnosis of aberrant immunity. Moreover, the fact that human IL-2 makes possible the in vitro proliferation of antigen specific human, mouse and rat killer T cells emphasizes the importance of human IL-2 as a research reagent.

The above cited articles by Morgan et al., 193 *Science* 1007 (1976); Ruscetti et al., 119 *The Journal of Immunology* 131 (1977); and Gillis et al., 124 *The Journal of Immunology* 1954 (1980), discuss production of human IL-2 from lectin stimulated human splenic and peripheral blood lymphocyte conditioned media. However, these production sources and techniques result in weak concentrations of IL-2, with purification of IL-2 requiring fractionation of large volumes of conditioned media containing IL-2 in order to obtain only very small quantities of human IL-2 activity. As a consequence, sufficient quantities of concentrated human IL-2 have not been available for in vivo experiments, nor to study effectively the final molecular characterization of this lymphocyte regulatory molecule.

U.S. Pat. No. 4,401,756, entitled "Process For Preparing Human Interleukin 2" inventor Steven Gillis describes the production of human IL-2 by induction of a malignant neoplastic cell line such as the Jurkat-FHCRC line with a T-cell mitogen such as phytohemagglutinin (PHA) optionally in the presence of a phorbol ester such as phorbol myristate (PMA). Partial purification of the IL-2 was achieved by a procedure involving ammonium sulfate precipitation/dialysis, gel filtration chromatography (Sephadex G-100), ion exchange chromatography DEAE cellulose), flat bed isoelectric focusing and analytical SDS polyacrylamide gel electrophoresis. The majority of IL-2 biological activity was electrophoretically eluted from the protein band (one of nine to sixteen separate bands observed on the gel) having a molecular weight of approximately 14,000 daltons. See also Frank et al. J. Immunol. 127, 2361 (1981) and Watson et al. Lymphokines 6, 95 (1982) for a corresponding disclosure.

Mier and Gallo, J. Immunol. 128, 1122 (1982) and also Lymphokines 6, 137 (1982) have reported on the purification of IL-2 from normal lymphocytes to provide "a nearly homogeneous material" using preparative SDS gel electrophoresis as the last step after a sequence of anion exchange chromatography and gel filtration procedures. Their product had a molecular weight of 13,000 on SDS-PAGE and 20–25,000 on gel filtration and an isoelectric point of 6.8. This material was very unstable even at −70° C. and required addition of BSA or polyethylene glycol to retain activity.

Stadler and Oppenheim, Lymphokines 6, 117 (1982) describe IL-2 purified from peripheral blood mononuclear cells, tonsil and spleen cells which exhibited charge heterogeneity after purification on column chromatography, gel filtration and electrofocusing. Three charge species having pI's of 6.5, 7.2 and 8.2 were found and the heterogenecity possibly attributed to differences in the degree of glycosylation. Reference is made on page 127 to the observation of Robb and Smith of a single charge species of IL-2 derived from the 3urkat cell line having a pI of 8.2 (Mol. Immunol. 1981 indicated to be in press).

DESCRIPTION OF THE INVENTION

The present invention relates to human IL-2 derived from induced human malignant cells which is purified to essential homogeneity using multiple reverse phase high performance liquid chromatography steps. The procedure utilized to produce the homogeneous IL-2 product of the present invention involves passing a crude IL-2 preparation through a reverse phase methyl or octyl bonded silica HPLC column, eluting protein with a n-propanol gradient in buffer, pooling active fractions as determined by assay and passing the pooled active fractions through a reverse phase diphenyl bonded silica HPLC column. In those instances where the crude preparation used is of relatively low titer it may be necessary to repeat one or more of the HPLC steps in order to achieve purification to homogeneity.

Crude IL-2 preparations are readily prepared by culturing malignant human neoplastic cells, such as human leukemia and lymphoma cells in vitro in a serum containing medium supplemented with various additives. The culture is stimulated by a T cell mitogen such as PHA thereby producing a supernate which contains IL-2. After a period of time, i.e., approximately 24 hours of incubation the supernate is collected and processed to purify the IL-2 into a more concentrated form. It is also desirable to utilize a phorbol ester such as PMA as an inducing agent either alone or in combination with a T-cell mitogen such as PHA or Con A to enhance the production of IL-2. For further details see Gillis et al. J. Exp. Med. 1:52, 1701 (1980).

Cell lines which can be employed in the production of crude human IL-2 include various T and B cell lines as well as various T lymphoma cell lines. The cell lines were produced by either spontaneous occurrence, vital infection or by chemical carcinogen. A preferred cell line for this purpose is identified by Gillis et al. supra as the Jurkat-FHCRC leukemic human T cell line and most preferably a sub-clone of this kine designated H33HJ-JA1. The process of the invention can also be used to purify IL-2 derived from peripheral blood lymphocytes.

The culture medium used to produce crude human IL-2 in conjunction with the aforesaid cell lines may consist of commercially available media, such as Dulbecco Modified Eagle Medium, RPMI medium and Click's medium. Additives which may be individually or in combination added to the culture medium include penicillin, streptomycin, gentamycin, fresh L-glutamine, HEPE5 buffer, $NaHCO_3$, fetal calf serum (FCS) or normal human serum. The initial cell density of cells, particularly when Jurkat-FHCRC cells are employed, should be in the range of about $5 \times 10^5$ cells/ml to $1 \times 10^7$ cells/ml, most preferably about $1 \times 10^6$ cells/ml.

Culture conditions include a temperature in the range of about 35° to 38° C., a pH in the range of 7.0 to 7.4 and a humidified atmosphere of from approximately 5 to 10% carbon dioxide in air. A PHA mitogen concentration in the range of 0.5% to 2.0% by volume, preferably 196 by volume may be used.

The quantity of IL-2 produced by stimulating malignant human cells with a plant mitogen varies with time. Peak levels of IL-2 are reached at approximately sixteen to twenty-four hours after stimulation by PHA. Assay of IL-2 for monitoring the cell culture production procedure or to monitor purification procedures involves assessing the capacity of the sample to induce T cell line proliferation. T cell proliferation is determined by measuring the incorporation of tritiated thymidine. One unit of activity is defined as the number of microliters present in a T cell culture well which induced 50% of maximal thyroidinc incorporation. Specific details of the assay procedure are set forth in Gillis et al. J. Immunol. 120, 2027 (1978) as well as the aforesaid U.S. patent application Ser. No. 249,905.

Preparation of a suitable starting material for carrying out the HPLC purification steps of the present invention involves, precipitating IL-2 containing supernates derived by centrifuging harvested induced cells by addition of ammonium sulfate to 85% saturation. Such addition is accomplished by the gradual addition of dry ammonium sulfate to the supernatant with gentle stirring. Addition of ammonium sulfate for precipitation is done over an extended period of time, e.g. a 12 hour period. Upon reaching 85% saturation the gentle stirring is continued for an addtitional period in the cold. The precipitated protein is pelleted by centrifugation and the pellets resuspended in sterile double distilled water.

In one alternate process aspect the resuspended crude IL-2 is subjected to ion exchange chromatography. A suitable column for this purpose is CM biogel A resin (LKB Productor, Broma, Sweden). Preferably the column is pretreated with a fetal calf serum solution to block non-specific binding sites on the resin before application of the IL-2 containing sample. Elution from the column is accomplished with a buffered salt gradient. A suitable gradient for this purpose is 50 mM–0.5M sodium chloride in HEPES pH 5.5. A final wash with 0.5M NaCl-HEPES pH 5.5 is used to ensure that all IL-2 activity is eluted.

Pooled active fractions from the above ion exchange chromatography step provides a preferred starting material for the HPLC procedures which form the process aspect of the present invention. In an alternative embodiment it is possible where sufficiently high titer supernatant from the ammonium sulfate step is available to use this material directly unto the first HPLC column step. However, in such aspect it may be necessary to repeat one or both of the HPLC steps in order to achieve essential homogeneity in the product IL-2.

The HPLC steps employed in the instant process use a reverse phase, methyl, octyl or diphenyl bonded silica column having a pore size of sufficient diameter to be optimally utilized with proteins, i.e., a pore size of at least about 150Å. Suitable reverse phase HPLC columns for use in the practice of the invention are articles of commerce. Particularly preferred for this purpose are the Protesil line of columns commerically available from Whatman Separations Inc., Clifton, N.J.

Thus, for example, Whatman Protesil 300 Methyl is a column consisting of trimethylsilyl groups covalently bonded by means of a silicon-oxygen-silicon bond to the surface of a 300 Angstrom pore diameter silica gel which has been classified to a mean particle size of 8 microns. In similar fashion the Whatman Protesil Magnum octyl column has octyl groups covalently bonded to 150 Angstrom pore diameter silica gel while the Whatman Protesil Diphenyl column has diphenyl groups covalently bonded to the surface of a 300 Angstrom silica gel.

The elution of proteins from the HPLC columns can be carried out in a manner known per se in the art. A suitable elution procedure for removing bound proteins from the methyl or octyl columns used in the first HPLC step of the present process involves the use of a gradient of increasing concentration of a water miscible lower alkanol, preferably n-propanol. A preferred gradient for this purpose is a 0–60% vol/vol gradient in pyridine-acetic acid pH 4.0.

Similar elution conditions may be employed in conjunction with the diphenyl column used in the second step with the exception that the lower alkanol gradient is 20–60% vol/vol. Eluted protein can conveniently be monitored with detection systems known in the art such as, for example, by use of an automated fluorescence detection system described by Stein and Moschera, Methods Enzymol. 78, 435 (1981).

After carrying out the HPLC process steps, either in two steps or where low titer crude is used, with one or more repeats of the first and/or second steps, IL-2 is obtained, purified to homogeneity as a single symmetrical peak of bioactivity in good yield.

The ability to prepare homogeneous IL-2 allows for the first time the determination of the amino acid composition and sequence of this molecule. This information, in turn, is important in assisting in the cloning of the human IL-2 gene and the ultimate production of large amounts of pure recombinant IL-2 for clinical trials and ultimately for widespread medical use of this substance. Moreover, the availability of homogeneous IL-2 will allow accurate biological studies of its activity free from the contamination of the numerous lymphokine species which are known to be co-produced with IL-2 during the inducation procedure. While the prior art has claimed to prepare highly purified or nearly homogeneous IL-2 preparations, experience has shown that when material indicated to be single band material on SDS-Page analytical electrophoresis is used as starting material in the instant HPLC process on a methyl or octyl column, the band is resolved into a large number of protein peaks which are unassociated with the IL-2 activity. Based on such observations it is believed that such preparations are no more than 10% pure and in some instances may even be less than 1% pure.

Tests with partially purified IL-2 preparations derived from Jurket-FHCRC cell line has determined that the partially purified lymphokine does not cause fresh peripheral blood lymphocytes to proliferate; but does induce profileration in T-lymphocyte populations previously stimulated with lectins or specific antigens. Moreover, partially purified human IL-2 was found to maintain the proliferation of not only human antigen-specific effector T-cells, but also murine antigen-specific effector T cells. Thus, Jurkat-FHCRC produced human IL-2, even partially purified has been shown to be a useful reagent for use in the growing of clonal human and murine T-cells with various antigens and effector specifications, and in fact is now an article of commerce for such uses. Homogeneous IL-2 of the present invention can, of course, be employed in similar manner.

The process and product of the present invention are further illustrated by the following Examples.

EXAMPLE 1

IL-2 Production

H33Ha-JAI cells (ATCC #CRL-8163, deposited Aug. 26, 1982) a clone of the parent Juckat-FHCRC cell line were grown in RPMI 1640 supplemented with 10% fetal calf serum, 50 U/ml penicillin, 50 µg/ml streptomycin, 50 µg/ml gentamycin and 300 µg/ml fresh L-glutamine. The cells were grown in 150 ml volumes in T 175 cm$^2$ flasks (Corning Plastics) at 37° C. in a humidified atmosphere of 5% $CO_2$ in air. Cells at saturation density (8–10×10$^5$ cells/ml) were harvested, centrifuged and resuspended in fresh RPMI 1640 medium without serum but containing 50 U/ml penicillin, 50 µg/ml streptomycin, 50 µg/ml gentamycin and 300 µg/ml fresh L-glutamine. Cells were resuspended to a concentration of 2×10$^6$ cells/mi. These cells were then placed in fresh T 175 cm$^2$ flasks (150 ml volume). Cells were stimulated by the addition of 1% PHA by volume (Gibco Diagnostics) and 10 ng/ml phorbol myristate acetate (PMA, Sigma Chemical Corp. St. Louis, Mo.). Following 24 hour incubation at 37° C. in a humidified atmosphere of 5% $CO_2$ in air, induced cells were harvested, centrifuged and the supernates retained as crude starting material.

Pooled supernatants from three cell culture runs (Numbers 1–3)comprising 900 ml, 900 ml and 1050 ml each or a total of 2,850 ml of supernatant, the pooled material having a total activity as determined by the assay of Gillis et al. J. Immunol. 120, 2027 (1978), of 7.125×10$^6$ Units, were treated by the gradual addition of dry ammonium sulfate to 85% saturation with gentle stirring. Addition of ammonium sulfate for precipitation was done over a 12 hour period. Once the solution reached 85% saturation gentle stirring was continued at 4° C. for an additional 24 hours. Protein present in the supernate was pelleted by a 30 minute centrifugation at 10,000×G. Supernates were decanted and discarded. The pellet was resuspended to 40 ml with double distilled sterile water and the resulting solution contained 205,000 U/ml of IL-2 or a total of 8.2× 10$^6$ Units. It should be noted that it is not unusual in several of the concentration and purification steps for the total activity to increase, Additional runs were carried out as summarized below in Table 1.

TABLE 1

| Run # | Supernatant Volume ml | Pooled Activity U/ml | Total Units × 10$^6$ | Resuspension Volume ml | Activity U/ml | Total Activity U × 10$^6$ |
|---|---|---|---|---|---|---|
| 4 | 1200 | 6500 | 9.425 | 55 | 200,000 | 11 |
| 5 | 250 | | | | | |
| 6 | 1200 | 6500 | 12.35 | 80 | 163,840 | 13.107 |
| 7 | 700 | | | | | |

(Bracketed Runs Were Pooled)

EXAMPLE 2

Ion Exchange Chromatography on CM Biogel A Column

A. Column preparation:

Column resin (CM Biogel A, LKB Productor, Broma, Sweden) was equilibrated in 0.05M NaCl-HEPES pH 5.5. the column (100 ml) was poured and one column volume (100 ml) of 0.05M NaCl-HEPES pH 5.5 containing 10% FCS as then applied to the column. This was done to block non-specific binding sites which could tie up human IL-2 activity. Serum proteins which bound to the column were then eluted off by the addition of 5 column volumes of 0.5M NaCl-HEPES pH 5.5. The column was then re-equilibrated with 10 volumes of 0.05M NaCl.

B. Sample Application and Chromatography

Combined resuspensions of ammonium sulfate precipitated protein comprising runs 1–5 of Example 1 was applied to the CM column The column was then washed with 2 column volumes of 0.05M NaCl-HEPES pH 5.5. A 500 ml salt gradient running from 50 mM to 0.5M NaCl-HEPES pH 5.5 was then applied to the column. After gradient application the column was washed with 200 ml of 0.5M NaCl-HEPES pH 5.5 to ensure that all bound IL-2 had indeed been eluted from the column. Fractions of 5 ml each were obtained. Every third fraction was assayed for IL-2 activity. Peak activity was determined and the active fractions pooled. There was thus obtained a pool of 36 ml having an activity of 983,040 U/ml or a total activity of $35.39 \times 10^6$ Units.

A second CM column run with the resuspended ammonium sulfate precipitates from pooled runs 6 and 7 of Example 1 provided pooled fractions having a volume of 215 ml, an activity of 80,000 U/ml and a total activity of $17.2 \times 10^6$ Units.

Lot A was prepared for further purification by combining the 36 ml derived from the first run and a 130 ml portion of the second thus providing 866 ml of crude IL-2 having a total of $10.4 \times 10^6$ Units when assayed on preparation.

EXAMPLE 3

Reverse Phase High Performance Liquid Chromatography with Octyl Column

Lot A obtained in Example 2 was pumped in toto directly onto a 9.4×250 mm Magnium 9 Protesil Octyl Column (Whatman Separations Inc., Clifton, N.J.) using a trace enrichment technique. The column was then washed with 50 ml of 0.9M acetic acid/0.2M pyridine pH 4.0 buffer. Elution of the proteins was accomplished with a gradient of n-propanol 0–60% vol/vol over 8 hours in the 0.9M acetic acid/0.2M pyridine pH 4 buffer. An automated fluorescence detection system using fluorescamine monitored the protein in the column effluents (Stein el al., supra). The recovery of biological activity was $7.13 \times 10^6$ Units (approx. 70%).

EXAMPLE 4

Reverse Phase High Performance Liquid Chromatography with Diphenyl Column

The fractions containing the major peaks of activity obtained in Example 3 were pooled, diluted 1:1 (v/v) with 0.9M acetic acid/0.2M pyridine pH 4.0 and pumped onto a 4.6×250 mm Whatman Protesil Diphenyl column. Proteins were eluted with a 20–60% n-propanol gradient in 0.9M acetic acid/0.2M pyridine, pH 4.0 buffer over 6½ hours. This procedure yielded a symmetrical peak coinciding with IL-2 activity. Recovery of activity in this step was greater than 60%. Essential homogeneity of this material was confirmed by analytical SDS-PAGE electrophoresis and two dimensional gel electrophoresis which yielded a single band and a single spot respectively.

Samples of this material were subject to amino acid analysis performed with fluorescamine detection (See Stein et al. Arch. Biochem. Biophy. 155, 203 (1973). The polypeptide was hydrolyzed for 24 and 48 hours at 104° C. In constant boiling HCl containing 0.1% thioglycolic acid. The results are summarized in Table 2 below:

TABLE 2

|     | 24 hours | 24 hours | 48 hours | Amino Acid Composition of IL-2 |
|-----|----------|----------|----------|-------------------------------|
| Asp | 12.3 | 11.8 | 11.8 | 12 |
| Thr | 8.6 | 9.6 | 7.4 | 10 |
| Ser | 7.5 | 5.2 | 7.3 | 8 |
| Glu | 18.3 | 15.4 | 16.0 | 16–17 |
| Pro | 9.7 | 10.7 | — | 8–9 |
| Gly | 7.5 | 6.3 | 10.8 | 8 |
| Ala | 7.5 | 6.0 | 8.4 | 7 |
| Cys |     |     |     | 4–5* |
| Val | 5.0 | 5.5 | 5.2 | 6 |
| Met | 4.3 | 3.3 | 3.1 | 4 |
| Ile | 5.0 | 7.5 | 6.3 | 7 |
| Leu | 13.7 | 19.4 | 16.0 | 16 |
| Tyr | 2.4 | 1.7 | 4.2 | 3 |
| Phe | 4.6 | 4.1 | 6.4 | 5 |
| His | 4.4 | 3.8 | 4.9 | 4 |
| Lys | 7.9 | 8.6 | 7.9 | 8 |
| Arg | 3.9 | 3.9 | 7.5 | 4 |
|     |     |     | Total | 130–133 |

*24 hour hydrolysis on separate sample

Homogeneous human IL-2 prepared as described above had a specific activity of about $1.4 \times 10^9$ U/mg and a pI of 5.68.

I claim:

1. Human interleukin 2 as a homogeneous protein characterized in having a specific activity of about $1.4 \times 10^9$ U/mg, a pI of about 5.68 and a composite amino acid composition as follows;

Asp - 12
Thr - 10
Ser - 8
Glu - 16–17
Pro - 8–9
Gly - 8
Ala - 7
Cys - 4–5
Val - 6
Met - 4
Ile - 7
Leu - 16
Tyr - 3
Phe - 5
His - 4
Lys - 8
Arg - 4.

2. Human interleukin 2 as a homogeneous protein.

* * * * *